US012144853B2

(12) United States Patent
Murphy et al.

(10) Patent No.: US 12,144,853 B2
(45) Date of Patent: Nov. 19, 2024

(54) TARGETED VACCINATION IN THE LIVER

(71) Applicant: UNIVERSITY OF WASHINGTON, Seattle, WA (US)

(72) Inventors: Sean C. Murphy, Seattle, WA (US); Bradley C. Stone, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 238 days.

(21) Appl. No.: 17/147,438

(22) Filed: Jan. 12, 2021

(65) Prior Publication Data

US 2021/0236615 A1 Aug. 5, 2021

Related U.S. Application Data

(60) Provisional application No. 62/960,499, filed on Jan. 13, 2020.

(51) Int. Cl.
*A61K 39/015* (2006.01)
*A61K 39/00* (2006.01)
*A61P 33/06* (2006.01)
*C07K 14/445* (2006.01)

(52) U.S. Cl.
CPC ............ *A61K 39/015* (2013.01); *A61P 33/06* (2018.01); *C07K 14/445* (2013.01); *A61K 2039/52* (2013.01); *A61K 2039/53* (2013.01); *A61K 2039/54* (2013.01); *A61K 2039/545* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 8,043,625 B2 | 10/2011 | Sim et al. |
| 8,367,810 B2 | 2/2013 | Sim et al. |
| 8,992,944 B2 | 3/2015 | Sim et al. |
| 9,241,982 B2 | 1/2016 | Sim et al. |
| 9,616,115 B2 | 4/2017 | Sim et al. |
| 10,272,146 B2 | 4/2019 | Sim et al. |
| 10,925,950 B2 | 2/2021 | Murphy et al. |
| 10,960,065 B2 | 3/2021 | Kurtis et al. |
| 11,168,307 B2 | 11/2021 | Paoletti et al. |
| 11,197,920 B2 | 12/2021 | Reyes-Sandoval |
| 2005/0244437 A1 | 11/2005 | Van Poppel et al. |
| 2012/0058180 A1 | 3/2012 | Kren et al. |
| 2017/0274061 A1 | 9/2017 | Sim et al. |
| 2017/0296481 A1 | 10/2017 | Bae et al. |
| 2018/0161413 A1 | 6/2018 | Eappen et al. |
| 2020/0338178 A1 | 10/2020 | Murphy et al. |
| 2021/0236615 A1 | 8/2021 | Murphy et al. |

FOREIGN PATENT DOCUMENTS

| | | |
|---|---|---|
| WO | 2004055187 A1 | 7/2004 |
| WO | 2005002512 A2 | 1/2005 |
| WO | 2012076157 A2 | 6/2012 |
| WO | 2015091734 A1 | 6/2015 |
| WO | 2016037916 A1 | 3/2016 |
| WO | 2016070082 A1 | 5/2016 |
| WO | 2017024084 A1 | 2/2017 |
| WO | 2019140136 A1 | 7/2019 |

OTHER PUBLICATIONS

Coppi et al. J. Exp. Med. 201: 27-33, 2005.*
Ferraro, B., et al. 2013 Inducing Humoral and Cellular Responses to Multiple Sporozoite and Liver-Stage Malaria Antigens Using Exogenous Plasmid DNA, 81(10): 3709-3720.
Longley, R.J., et al. 2015 Comparative assessment of vaccine vectors encoding ten malaria antigens identifies two protective liver-stage candidates, 5:11820 10.1038/srep 11820. 13 pages.
Pichugin, A., et al. 2018 Identification of a Novel CD8 T Cell Epitope Derived from Plasmodium berghei Protective Liver-Stage Antigen, 9(91). 12 pages.
Shears, M. J., et al. 2019 A New Non-Human Primate Model For Testing Human Malaria Vaccine Efficacy, 101(5): pp. 131, abstract 428.
ISA, International Search Report and Written Opinion for International Patent Application No. PCT/US2019/013114. Mail Date: Jun. 3, 2019. 15 pages.
Arrington, J., et al. 2002 Plasmid vectors encoding cholera toxin or the heat-labile enterotoxin from *Escherichia coli* are strong adjuvants for DNA vaccines J Virol 76:4536-4546.

(Continued)

*Primary Examiner* — S. Devi
(74) *Attorney, Agent, or Firm* — Perkins Coie LLP

(57) ABSTRACT

In one aspect, the present disclosure provides a trapping vaccine composition comprising a trapping antigenic component, a protective component, and a liver cell-targeting component, wherein the trapping antigenic component comprises a nucleic acid molecule or a protein, the protective component comprises a synthetic or non-natural molecule or formation of synthetic or non-natural molecules, and wherein the liver cell-targeting component is capable of delivering the vaccine composition to a liver cell or liver tissue. The present disclosure additional provides vaccination methods comprising (i) administering a priming composition comprising a priming antigenic component or a first dose comprising the priming composition to the mammal; and (ii) administering a trapping composition comprising a trapping antigenic component, a protective component, and a liver cell-targeting component, or a second dose comprising the second composition to the mammal, wherein the priming and trapping compositions or doses are not administered concurrently and wherein the number of resident memory T cells in the liver are increased following administration of the trapping composition. In certain embodiments, vaccine compositions and regimes are provided that protect against liver-tropic pathogens, e.g., a malarial infection. In an embodiment, a vaccine composition and regimen are provided that protect against an infection caused by *P. falciparum* or *P. yoelli* sporozoites.

11 Claims, 3 Drawing Sheets

(56) References Cited

OTHER PUBLICATIONS

Balam, S., et al. 2012 CSP-A Model for In Vivo Presentation of Plasmodium berghei Sporozoite Antigens by Hepatocytes PloS ONE 7(12):e51875. 8 pages.

Bauza, K., et al. 2015 Tailoring a Combination Preerythrocytic Malaria Vaccine Infect Immun 84:622-634.

Billman, Z.P., et al. 2016 Defining rules of CD8(+) T cell expansion against pre-erythrocytic Plasmodium antigens in sporozoite-immunized mice Malaria Journal 15:238. 13 pages.

Billman, Z.P., et al. 2016 Purification of Plasmodium Sporozoites Enhances Parasite-Specific CD8+ T Cell Responses Infect Immun 84:2233-2242.

Blom, K.G., et al. 2009 Isolation of murine intrahepatic immune cells employing a modified procedure for mechanical disruption and functional characterization of the B, T and natural killer T cells obtained Clin Exp Immunol 155:320-329.

Bongfen, S.E., et al. 2007. Plasmodium berghei-infected primary hepatocytes process and present the circumsporozoite protein to specific CD8+ T cells in vitro J Immunol 178:7054-7063.

Chen, L., et al. 2014 Identification of pre-erythrocytic malaria antigens that target hepatocytes for killing in vivo and contribute to protection elicited by whole parasite vaccination PloS one 9:e102225. 12 pages.

Cherif, M. et al. 2014 "Nanoparticle formulation enhanced protective immunity provoked by PYGPI8p-transamidase related protein (PyTAM) DNA vaccine in Plasmodium yoelii malaria model" Vaccine 32: 1998-2006.

Doolan, D.L., et al. 2000 The complexity of protective immunity against liver-stage malaria J Immunol 165:1453-1462.

Dunachie, S.J., et al. 2006 A DNA prime-modified vaccinia virus ankara boost vaccine encoding thrombospondin-related adhesion protein but not circumsporozoite protein partially protects healthy malaria-naive adults against Plasmodium falciparum sporozoite challenge. Infect Immun 74:5933-5942.

Fernandez-Ruiz, D., et al. 2016 Liver-Resident Memory CD8+ T Cells Form a Front-Line Defense against Malaria Liver-Stage Infection Immunity 45:889-902.

Gola, A. et al. 2018 Prime and target immunization protects against liver-stage malaria in mice Science Translational Medicine, 10: 11 pages.

Gorad, R. et al. 2013 Liver Specific Drug Targeting Strategies: A Review ISJPSR, 4(11): 4145-4157.

Gruner, A.C., et al. 2007 Sterile protection against malaria is independent of immune responses to the circumsporozoite protein. PloS one 2:e1371. 6 pages.

Haddad, D., et al. 2004. Novel antigen identification method for discovery of protective malaria antigens by rapid testing of DNA vaccines encoding exons from the parasite genome Infection and immunity 72:1594-1602.

Herweijer, H., et al. 2007 Gene therapy progress and prospects: hydrodynamic gene delivery Gene therapy 14:99-107.

Ishizuka, A.S., et al. 2016 Protection against malaria at 1 year and immune correlates following PfSPZ vaccination Nat Med 22:614-623.

Keitany, G.J., et al. 2014 Immunization of mice with live-attenuated late liver stage-arresting Plasmodium yoelii parasites generates protective antibody responses to preerythrocytic stages of malaria Infect Immun 82:5143-5153.

Kennedy, M., et al. 2012 A rapid and scalable density gradient purification method for Plasmodium sporozoites Malaria journal 11:421.

Kim, K. et al. 2018 Immense Insulin Intestinal Uptake and Lymphatic Transport Using Bile Acid Conjugated Partially Uncapped Liposome Molecular Pharmaceutics, 15(10), pp. 4756-4763.

Kiniry, B.E., et al. 2017 Detection of HIV-1-specific gastrointestinal tissue resident CD8(+) T-cells in chronic infection Mucosal Immunol 11:909-920.

Kovacsics, D., et al. 2014 Transient expression of proteins by hydrodynamic gene delivery in mice Journal of visualized experiments : JoVE 87: e51481.

Kumar, K.A., et al. 2006 The circumsporozoite protein is an immunodominant protective antigen in irradiated sporozoites Nature 444:937-940.

Kumar, K.A., et al. 2009 Conserved protective mechanisms in radiation and genetically attenuated uis3(-) and uis4(-) Plasmodium sporozoites. PloS one 4:e4480. 5 pages.

Lau, L.S., et al. 2011 Blood-stage Plasmodium berghei infection generates a potent, specific CD8+ T-cell response despite residence largely in cells lacking MHC I processing machinery The Journal of infectious diseases 204:1989-1996.

Liehl, P., et al. 2015 Innate immunity induced by Plasmodium liver infection inhibits malaria reinfections Infection and immunity 83:1172-1180.

Limbach, K., et al. 2011 Identification of two new protective pre-erythrocytic malaria vaccine antigen candidates Malaria journal 10:65.

Longley, R.J., et al. 2015 Development of an in vitro assay and demonstration of Plasmodium berghei liver-stage inhibition by TRAP-specific CD8+ T cells PloS one 10:e0119880.

Lyke, K.E., et al. 2017 Attenuated PfSPZ Vaccine induces straintranscending T cells and durable protection against heterologous controlled human malaria infection. Proc Natl Acad Sci USA 114:2711-2716.

Mauduit, M., et al. 2009 A role for immune responses against non-CS components in the cross-species protection induced by immunization with irradiated malaria sporozoites PloS one 4:e7717. 12 pages.

Mauduit, M., et al. 2010 Minimal role for the circumsporozoite protein in the induction of sterile immunity by vaccination with live rodent malaria sporozoites Infect Immun 78:2182-2188.

Mishra, S., et al. 2011 Identification of non-CSP antigens bearing CD8 epitopes in mice immunized with irradiated sporozoites Vaccine 29:7335-7342.

Moorthy, V.S., et al. 2003 Safety of DNA and modified vaccinia virus Ankara vaccines against liver-stage P. falciparum malaria in non-immune volunteers Vaccine 21:1995-2002.

Mordmuller, B., et al. 2017 Sterile protection against human malaria by chemoattenuated PfSPZ vaccine Nature, 542:445-449 + additional data.

Murphy, S.C., et al. 2013 A T-cell response to a liverstage Plasmodium antigen is not boosted by repeated sporozoite immunizations Proc Natl Acad Sci U S A 110:6055-6060.

Nurunnabi, Md., et al. 2017 Oral delivery of a therapeutic gene encoding glucagon-like peptide 1 to treat high fat diet-induced diabetes Journal of Controlled Release, 268: 305-313.

Olsen, T. et al. 2018 Prime-and-Trap Malaria Vaccination To Generate Protective CD8+ Liver-Resident Memory T Cells J Immunol, 201: 1984-1993.

Pavelko, K.D., et al. 2017 B7-H1 Influences the Accumulation of Virus-Specific Tissue Resident Memory T Cells in the Central Nervous System Front Immunol 8:1532.

Pearson, F.E., et al. 2015 Induction of CD8(+) T cell responses and protective efficacy following microneedle-mediated delivery of a live adenovirus-vectored malaria vaccine Vaccine 33:3248-3255.

Regules, J.A., et al. 2011 The RTS,S vaccine candidate for malaria Expert Rev Vaccines 10:589-599.

Renia, L., et al. 1993 Effector functions of circumsporozoite peptide-primed CD4+ T cell clones against Plasmodium yoelii liver stages J Immunol 150:1471-1478.

Richie, T.L., et al. 2012 Clinical trial in healthy malaria-naive adults to evaluate the safety, tolerability, immunogenicity and efficacy of MuStDO5, a five-gene, sporozoite/hepatic stage Plasmodium falciparum DNA vaccine combined with escalating dose human GM-CSF DNA Hum Vaccin Immunother 8:1564-1584.

Rodrigues, M.M., et al. 1991 CD8+ cytolytic T cell clones derived against the Plasmodium yoelii circumsporozoite protein protect against malaria Int Immunol 3:579-585.

Romero, P., et al. 1989 Cloned cytotoxic T cells recognize an epitope in the circumsporozoite protein and protect against malaria Nature 341:323-326.

(56) References Cited

OTHER PUBLICATIONS

Sauzet, J.P., et al. 2001 DNA immunization by Plasmodium falciparum liver-stage antigen 3 induces protection against Plasmodium yoelii sporozoite challenge Infection and immunity 69:1202-1206.

Schmidt, N.W., et al. 2010 Extreme CD8 T cell requirements for anti-malarial liver-stage immunity following immunization with radiation attenuated sporozoites PLoS Pathog 6:e1000998. 15 pages.

Schmidt, N.W., et al. 2008 Memory CD8 T cell responses exceeding a large but definable threshold provide long-term immunity to malaria Proc Natl Acad Sci U S A 105:14017-14022.

Seder, R.A., et al. 2013 Protection against malaria by intravenous immunization with a nonreplicating sporozoite vaccine Science 341:1359-1365.

Spencer, A.J., et al. 2017. The Threshold of Protection from Liver-Stage Malaria Relies on a Fine Balance between the Number of Infected Hepatocytes and Effector CD8(+) T Cells Present in the Liver J Immunol 198:2006-2016.

Strutt, T.M., et al. 2017 IL-15 supports the generation of protective lung-resident memory CD4 T cells Mucosal Immunology, 11(3), 668-680.

Tan, H.X., et al. 2017 Induction of vaginal-resident HIV-specific CD8 T cells with mucosal prime-boost immunization Mucosal Immunol. 15 pages.

Tse, S.W., et al. 2013. Unique transcriptional profile of liver-resident memory CD8+ T cells induced by immunization with malaria sporozoites Genes Immun 14:302-309.

White, K.L., et al. 1996. MHC class I-dependent presentation of exoerythrocytic antigens to CD8+ T lymphocytes is required for protective immunity against Plasmodium berghei J Immunol 156:3374-3381.

WHO. 2016. World Malaria Report 2016. 186 pages.

Wu, S. et al. 2019 "A Delivery System for Oral Administration of Proteins/Peptides Through Bile Acid Transport Channels" Journal of Pharmaceutical Sciences: 2143-2152.

Zhang, Y., et al. 2012. A new malaria antigen produces partial protection against Plasmodium yoelii challenge Parasitology research 110:1337-1345.

Zhang, Z., et al. 2018 Liver-targeted delivery of insulin-loaded nanoparticles via enterohepatic circulation of bile acids Drug Delivery, 25(1): 1224-1233.

CDC, 2017 Recommended Immunization Schedule for Children and Adolescents Aged 18 Years or Younger, 1-8.

Doll et al., 2016 Discriminating Protective from Nonprotective Plasmodium-Specific CD8+ T Cell Responses, Journal of Immunology, 196(10): 4253-4262.

Kitchen et al., 2006 Malaria and blood transfusion, Vox Sanguinis, 90: 77-84.

Laurens, 2018 The Promise of a Malaria Vaccine-Are We Closer, Annual Reviews Microbiology, 72: 273-292.

Le et al., 2000 Safety, tolerability and humoral immune responses after intramuscular administration of a malaria DNA vaccine to healthy adult volunteers, Vaccine, 18: 1893-1901.

Liu et al., 2017 Plasmodium parasite as an effective hepatocellular carcinoma antigen glypican-3 delivery vector, Oncotarget, 8(15): 24785-24796.

USPTO, Non-Final Office Action for U.S. Appl. No. 16/946,861. Mail Date: Jan. 23, 2023. 23 pages.

USPTO, Non-Final Office Action for U.S. Appl. No. 16/946,861. Mail Date: Jun. 7, 2022. 24 pages.

Bergmann-Leitner et al. 2007, "C3d-defined complement receptor-binding peptide p28 conjugated to circumsporozoite protein provides protection against Plasmodium berghei", Sep. 4, 2007, Vaccine, vol. 25, p. 7732-7736.

Billman et al. 2016, "Defining rules of CD8+ T cell expansion against pre-erythrocytic Plasmodium antigens in sporozoite-immunized mice", 2016, Malaria Journal, vol. 15, Article 238, p. 1-13.

Chuang et al. 2013 "DNA Prime/Adenovirus Boost Malaria Vaccine Encoding P. falciparum CSP and AMA1 Induces Sterile Protection Associated with Cell-Mediated Immunity", Feb. 14, 2013, PLOS ONE, vol. 8, Issue 2, Article e55571, p. 1-15.

Niidome et al. 2002 "Gene Therapy Progress and Prospects: Nonviral vectors", 2002, Gene Therapy, vol. 9, p. 1647-1652.

USPTO, Final Office Action for U.S. Appl. No. 16/946,861. Mail Date: Aug. 28, 2023. 22 pages.

\* cited by examiner

TARGETED VACCINATION IN THE LIVER

PRIORITY CLAIM

This application claims priority to U.S. Provisional Application No. 62/960,499, filed Jan. 13, 2020, which is incorporated herein by reference in its entirety, including drawings.

STATEMENT REGARDING FEDERALLY SPONSORED RESEARCH

The present invention was made with government support under grant number R01AI141857, awarded by the National Institutes of Health. The government may have certain rights in the invention.

BACKGROUND

Effective T cell vaccines against malaria act against the liver stage of the parasite. We and others recently showed that this is achieved through liver resident memory T cells. Our prime-and-trap vaccine strategy combined DNA priming vaccination in the skin with an attenuated sporozoite booster vaccination delivered intravenously, a combination that achieves a potent and protective intra-hepatic response. (Olsen et al. 2018). However, sporozoites must be manufactured in mosquitoes and must be delivered intravenously. Another method utilizes intravenous delivery of virus-based vaccines for liver targeting. However, all such methods have drawbacks (manufacturing, delivery, safety). There is a need for an inexpensive, wholly-synthetic, easily delivered and protective vaccine, or vaccine regimen. Orally deliverable vaccines, especially as the trap vaccination of a prime-and-trap vaccine strategy, would be particularly advantageous over current approaches to malarial vaccinations.

Antibodies (Ab) and cytotoxic T lymphocytes (CTL) contribute to sterile protection at the pre-erythrocytic stage by blocking invasion (Ab, Keitany et al. 2014) and killing infected hepatocytes (CTL, Doolan and Hoffman), respectively. CTL that kill infected hepatocytes before release of viable merozoites (Doolan and Hoffman) are important for complete protection. However, thus far, durable sterile protection has only been achieved by repeated immunization with live attenuated sporozoites that arrest in the liver. Importantly, these sporozoite vaccines must be manufactured in mosquitoes and delivered by multiple intravenous (IV) injections.

Pre-clinical work showed that repeated sporozoite immunization resulted in stepwise reductions in liver burden at the time of vaccination dosing. This reduced infectivity of sequential vaccine booster doses was accompanied by reduced boosting against multiple T cell target antigens. Notably, clinical trials have shown a lack of CTL boosting for many antigens after the first sporozoite immunization (e.g., Mordmuller et al., 2017).

Antigen-specific responses have been minimally studied in humans since the outbred nature of human MHC makes epitope prediction difficult. Instead, inbred mice are valuable for understanding the expansion and contraction of specific T cell populations in responses to antigen presentation. Across both BALB/c (Murphy et al. 2013) and C57BL/6 (Billman et al. 2016) backgrounds, the collective data now show that antigen-specific CD8$^+$ T cell responses to PyL3, PbS20$_{318-326}$, PbGAP50$_{41-48}$, PbF4, and PbNCY contract despite repeated immunization whereas responses to protective TRAP and CSP antigens remain stable or even expand. Responses that contract do not exclusively target late liver stage antigens. These data show that repeated sporozoite immunization results in a progressively more protective total immune response accompanied by a gradual 'debulking' of subsequent vaccine doses. This debulking explains the lack of secondary expansion of T cells targeting proteins like L3, F4 and NCY and possibly also S20. Debulking is at least partly due to antibodies directed against homologous parasites at the vaccination time point since circumventing such antibodies with heterologous sporozoites increased liver burden upon secondary vaccination (Billman et al. 2016). These model antigens are likely emblematic of an entire class of antigens that fail to re-expand due to debulking of the secondary and later immunization doses by the immunity achieved by primary immunization. In summary, each successive booster dose of attenuated sporozoites is less and less effective, due in large part to transmission blocking antibodies induced by earlier sporozoites doses.

T cells residing in the liver are known as liver resident memory T cells. It is generally thought that when effector T cells encounter antigen in non-lymphoid tissues, a subset undergo transcriptional changes and differentially express cell-surface markers that restrict migration to the local milieu thus informing such T cells to remain as Trm. In the liver, Trm seeding can occur without overt inflammation (i.e. by antigen alone in the absence of an infectious agent). In the past year, CD8$^+$ Trm cells were identified in pre-clinical *Plasmodium* studies as key components of pre-erythrocytic protection (Fernandez-Ruiz et al. 2016).

Repeated immunizations with attenuated sporozoites are known to induce CTLs that establish liver Trm (Fernandez-Ruiz et al. 2016) and that vaccine-induced cells can directly kill parasite-infected hepatocytes (Doolan and Hoffman; White et al. 1996).

In humans, samples can only be obtained from peripheral blood. At the conclusion of vaccination, total sporozoite-specific cytokine-producing CD8$^+$ T cells are more abundant in persons who go on to be protected against challenge as compared to those who are not protected (Seder et al.). However, the total percentage of parasite-specific cells in the periphery is extremely low (<0.5% of CD8s). Moreover, these T cell frequencies are lower than after the first sporozoite vaccination such that there is not apparent boosting of peripherally-measured T cell responses beyond the peak observed after the first dose of vaccine (Ishizuka et al.; Lyke et al.). Nonetheless, sporozoite-vaccinated human subjects can be protected at more than one-year post-vaccination at a time when parasite-specific antibody titers are low and non-protective (Ishizuka et al.). Thus, human data supports the idea that although antibodies may play a role in short term protection, liver resident memory T cells (Trm) are essential for long-term sterile protection (Ishizuka et al.). Although Trm cannot be measured directly in humans, they have been measured in mice and non-human primate livers. Parasite-specific, cytokine-producing CD8$^+$ T cells in the livers of vaccinated animals were >10-100 times more abundant than the same cells in peripheral blood (Ishizuka et al.). Accordingly, the correlate of immunity in humans may be in the liver, an unmeasurable compartment.

Dendritic cell (DC) priming induced CD8$^+$ T cells that could later be trapped in the liver using viral vectors that induced liver inflammation and parasite-specific antigen expression by hepatocytes (Fernandez-Ruiz et al.). These trapped cells form liver Trm, which were required for protection against malaria sporozoite challenge. Tissue resident memory T cells are increasingly appreciated in a wide array of organs including the lung (Strutt et al.), liver (Fernandez-Ruiz et al.; Tse et al.), central nervous system (Pavelko et al.), gastrointestinal tract (Kiniry et al.) and genital tract (Tan et al.).

Thus, vaccines capable of efficiently inducing liver Trm CTL for or other liver-tropic pathogens would be highly desirable. A completely protective vaccine is urgently needed to reduce the burden of disease and to accelerate progress toward elimination of infections. However, progress toward a vaccine has been difficult and as such, it is of importance to develop alternative methods for vaccinating subjects against liver-tropic pathogens, including malaria.

SUMMARY

In accordance with the vaccine composition embodiments, vaccine regimen embodiments, and methods of vaccinating embodiments described herein, the present disclosure provides a trapping vaccine composition comprising a trapping antigenic component, a protective component, and a liver cell-targeting component, wherein the trapping antigenic component comprises a nucleic acid molecule or a protein, the protective component comprises a synthetic or non-natural molecule or formation of synthetic or non-natural molecules, and wherein the liver cell-targeting component is capable of delivering the vaccine composition to a liver cell or liver tissue. In some embodiments, the trapping antigenic component is encompassed by, enveloped by, encapsulated by, coated by, or intercalated with or forms a polyplex with the protective component. In another embodiment, the trapping antigenic component comprises a nucleic acid molecule under control of a liver-specific promoter.

In an aspect of the vaccine compositions, vaccine regimens, and methods of vaccinating described herein, the present disclosure provides vaccine compositions comprising a trapping antigenic component wherein the trapping antigenic component is a virus, a plasmid, a nucleic acid molecule (naked nucleic acid), a deoxynucleic acid (DNA) molecule, a ribonucleic acid (RNA) molecule, a protein, a peptide, or a plurality thereof. In an aspect, the virus, plasmid, nucleic acid molecule, deoxynucleic acid (DNA) molecule, ribonucleic acid (RNA) molecule, protein, peptide molecule, or plurality thereof comprises a portion of the nucleic acid, peptide, or protein of a *Plasmodium* parasite.

In an aspect of the vaccine compositions, vaccine regimens, and methods of vaccinating described herein, the present disclosure provides vaccine compositions comprising a trapping antigenic component wherein the trapping antigenic component comprises a protein or peptide derived from a *Plasmodium* parasite or a portion thereof or a nucleic acid sequence encoding a protein or peptide derived from a *Plasmodium* parasite, wherein the *Plasmodium* parasite is selected from: a) *Plasmodium falciparum* circumsporozoite protein; b) *Plasmodium vivax* circumsporozoite protein; c) *Plasmodium falciparum* TRAP/SSP2 protein; d) *Plasmodium vivax* TRAP; e) *Plasmodium falciparum* AMA1; and f) *Plasmodium falciparum* LSA-1.

In some embodiments of the vaccine compositions, vaccine regimens, and methods of vaccinating described herein, the present disclosure provides vaccine compositions comprising a protective component selected from one or more of: a) particles; b) nanoparticles; c) liposomes; d) nanosomes; e) niosomes; and f) microparticles. In an embodiment, the protective component is conjugated to a liver cell-targeting component selected from one or more of: a) bile acid-conjugated, chitosan-containing particles or nanoparticles (e.g., plasmid DNA or mRNA as chitosan particles coated with or formulated with bile acids); b) non-bile acid-conjugated, chitosan-containing particles or nanoparticles coated with or formulated with a different liver-targeting formulation; c) bile acid-conjugated, non-chitosan-containing particles or nanoparticles (e.g., plasmid DNA or mRNA with branched polyethyleneimine followed by coating the surface with bile acid conjugates); and d) non-bile acid-conjugated, non-chitosan-containing particles or nanoparticles coated with or formulated with a different liver-targeting formulation.

In an aspect of the vaccine compositions, vaccine regimens, and methods of vaccinating described herein, the present disclosure provides an oral vaccine composition comprising any of the vaccine compositions.

In an aspect of the vaccine compositions, vaccine regimens, and methods of vaccinating described herein, the present disclosure provides vaccine compositions wherein the vaccine composition is the trap vaccine (or second dose) of a prime-and-trap vaccine regimen.

In an aspect of the vaccine compositions, vaccine regimens, and methods of vaccinating described herein, the present disclosure provides a vaccination regimen (e.g., a malarial vaccination regimen) comprising: (i) a priming composition comprising a priming antigenic component or a first dose comprising the priming composition, and (ii) a trapping composition comprising a trapping vaccine composition described herein or a second dose comprising the trapping composition. In an embodiment, the priming antigenic component and the trapping antigenic component of the trapping composition are the same or different molecules. In an embodiment, the priming composition is administered to the skin of a mammal. In embodiments, the priming composition is administered intradermally, transdermally, or epidermal. In an embodiment, the trapping composition is administered orally.

In an aspect of the vaccine compositions, vaccine regimens, and methods of vaccinating described herein, the present disclosure provides a vaccination regimen comprising: (i) a priming composition comprising a priming antigenic component or a first dose comprising the priming composition, and (ii) a trapping composition comprising the trapping compositions described herein or a second dose comprising the trapping composition, wherein the priming antigenic component is selected from the group consisting of: (a) a wild-type or an attenuated *Plasmodium* parasite; (b) a deoxyribonucleic acid (DNA) polynucleotide; (c) a ribonucleic acid (RNA) polynucleotide; (d) a protein or a polypeptide; (e) a virally-vectored antigen; (f) a virus-like particle delivered antigen; (g) a nanoparticle; (h) a fragment of any of (b), (c), (d), (e), or (f); (i) a subunit of (e) or (f); and (j) a combination of any of (a), (b), (c), (d), (e), (f), (g), or (h).

In an aspect of the vaccine compositions, vaccine regimens, and methods of vaccinating described herein, the present disclosure provides a method of vaccinating a subject, comprising the steps of: (i) administering a priming composition comprising a priming antigenic component or a first dose comprising the priming composition to the subject; and (ii) administering a trapping composition comprising a trapping vaccine composition of the present disclosure or a second dose comprising the trapping composition to the subject; wherein the priming and trapping compositions or doses are not administered concurrently and wherein the number of resident memory T cells in the liver are increased following administration of the trapping composition. In an embodiment, the priming antigenic component and the trapping antigenic component of the trapping composition are the same or different molecules. In another embodiment, the priming antigenic subunit component is selected from the group consisting of: (a) a wildtype or an attenuated *Plasmodium* parasite; (b) a deoxyribonucleic acid (DNA) polynucleotide; (c) a ribonucleic acid (RNA) polynucleotide; (d) a protein or a polypeptide; (e) a virally-vectored antigen; (f) a virus-like particle delivered antigen; (g) a nanoparticle; (h) a fragment of any of (b), (c), (d), (e), or (f); (i) a subunit of (e) or (f); and (j) a combination of any of (a), (b), (c), (d), (e), (f), (g), or (h).

In an aspect of the vaccine compositions, vaccine regimens, and methods of vaccinating described herein, the present disclosure provides for any of the antigenic component or antigenic subunits to comprise a tag. In an embodiment the tag is a ubiquitin tag.

In an aspect of the vaccine compositions, vaccine regimens, and methods of vaccinating described herein, the present disclosure provides for the addition of an adjuvant the vaccine compositions, vaccine regimens, or vaccine methods.

DETAILED DESCRIPTION

Figure 1:
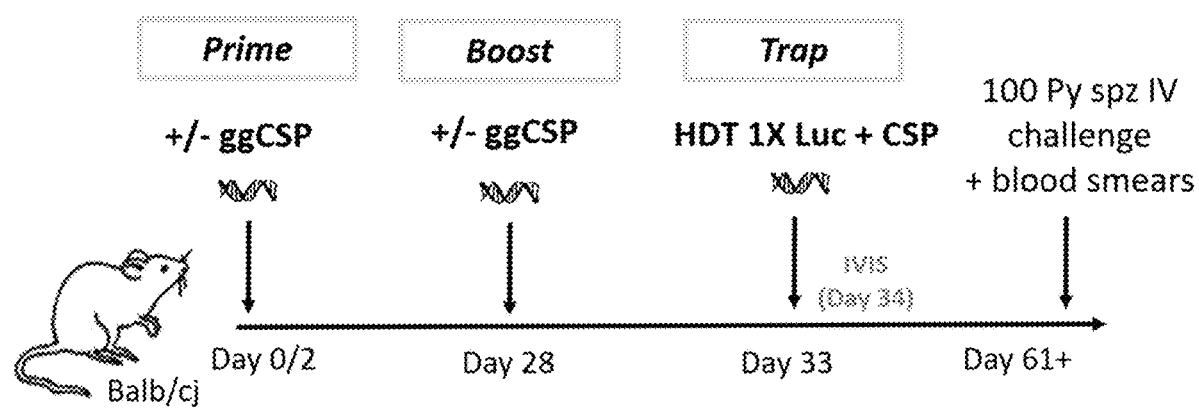
FIG. 1 is a schematic overview showing experimental design of a dose de-escalation study to examine the effects of PyCSP DNA given by hydrodynamic transfection (HDT) protect following a challenge with a physiologically-relevant IV dose of *P. yoelii* sporozoites (100 Py sporozoites).

The present technology is directed generally to vaccine compositions, delivery regimens, methods of administration, associated methods, and associated systems for protecting against a liver-tropic pathogen, e.g., a malarial infection or a hepatitis C infection. Without wishing to be bound by a particular theory, it is thought that one or more vaccine components can work for recruitment of resident memory T cells in the liver to protect a subject, such as a human or any other mammal, against an infection caused by a liver-tropic pathogen, e.g., a malarial infection or a hepatitis C infection. The recruitment of resident memory T cells is induced by a "prime-and-trap" vaccination strategy. This prime-and-trap strategy has been previously described in Tayla M. Olsen, Brad C. Stone, Vorada Chuenchob and Sean Murphy; J Immunol 2018; 201:1984-1993, and PCT application NO. PCT/US19/13114 filed on Jan. 10, 2019, which claims priority to U.S. Provisional application No. 62/615,755 filed Jan. 10, 2018, all of which are incorporated herein by reference for their teachings of the prime-and-trap strategy and for the compositions and methods of making a "priming" composition (also referred to herein as "priming vaccine" composition or "first composition" that may be used as a "first dose"), and for the compositions and methods of making a trap, i.e., the "trapping" composition (also referred to herein as a "trapping vaccine" composition or "liver-targeting vaccine" composition, or "second composition" that may be used as a "second dose").

Vaccine Compositions

The embodiments described herein utilize a modified prime-and-trap approach. The first or priming composition includes a priming antigenic component that is able to elicit (or "prime") an immune response against an antigenic portion priming antigenic component. The second or trapping composition includes (i) a second or trapping antigenic component to boost or bolster the effects of the priming component, (ii) a protective component or carrier for the antigenic component (in some aspects the carrier may be part of the antigenic component, e.g., a viral vector or VLP) and (iii) a trapping component that directs (or traps) the antigenic subunit to a target tissue (e.g., liver). In certain embodiments, the trapping component described herein is a liver-specific antigenic component.

Specific details of some embodiments of the present technology are described below with reference to vaccine compositions, vaccination regimens, and/or methods for administering one or more of the vaccine compositions and/or vaccination regimens to a subject in need, and associated systems for determining certain aspects of the methods. Some embodiments can have configurations, components and/or procedures different than those which are described herein, and other embodiments may eliminate particular components or procedures.

Priming Compositions

According to the embodiments described herein, a priming vaccine composition includes a priming antigenic component able to elicit an immune response when administered systemically. Priming vaccine compositions that may be used in accordance with the embodiments described herein are taught in detail in Tayla M. Olsen, Brad C. Stone, Vorada Chuenchob and Sean Murphy; J Immunol 2018; 201:1984-1993, and in PCT application NO. PCT/US19/13114 filed on Jan. 10, 2019, which claims priority to U.S. Provisional application No. 62/615,755 filed Jan. 10, 2018, all of which are incorporated herein by reference as if fully set forth herein.

In certain embodiments, the priming antigenic component may be a protein, peptide, or antigenic portion thereof expressed by a virus, a virus-like particle (VLP) or a plasmid; a plasmid that encodes a nucleic acid molecule, a deoxynucleic acid (DNA) molecule (or polynucleotide), or a ribonucleic acid (RNA) molecule (or polynucleotide); or a DNA molecule, an RNA molecule (or polynucleotide), a protein, a polypeptide, a peptide, or antigenic portions or combinations thereof. In some embodiments where the priming antigenic component is a virus, a VLP, or plasmid, said virus, VLP, or plasmid comprises or encodes the nucleic acid molecule, DNA molecule or polynucleotide, RNA molecule or polynucleotide, protein, or peptide used as a priming antigenic component. In certain embodiments, the priming antigenic component may also need a delivery vehicle or carrier to effect expression of the antigen. For example, a vaccine composition that uses an RNA or DNA molecule (e.g., as part of a plasmid) for the antigenic component needs to be delivered intracellularly to the cytoplasm or nucleus, respectively, of a target cell. Thus, in some embodiments, the RNA or DNA molecule may be delivered by a viral vector, a VLP, a nanoparticle, or any other suitable delivery vehicle or carrier (e.g., particles, liposomes, nanosomes, niosomes, microparticles). Consequently, in certain embodiments, the priming antigenic component can be a deoxyribonucleic acid (DNA) polynucleotide (e.g., a plasmid), a ribonucleic acid (RNA) polynucleotide, a protein or a polypeptide, a virally-vectored antigen, a virus-like particle delivered antigen, a nanoparticle, a fragment thereof, a subunit thereof, and/or a combination thereof.

In some embodiments, the nucleic acid molecule, DNA molecule, RNA molecule, protein, or peptide used as a priming antigenic component may be derived from a liver-tropic pathogen that gives rise to a hepatotropic infection or a pathogenic marker expressed on liver cells (e.g., cancer-specific markers), examples of which are discussed below.

In some embodiments, the priming antigenic component is a wildtype or an attenuated *Plasmodium* parasite. In some embodiments, the wild-type or attenuated *Plasmodium* parasite is a wild-type or attenuated sporozoite from a species of malaria. For example, the priming antigenic component of the priming composition includes one or more wild-type or attenuated sporozoites selected from one or more *Plasmodium* species, such as but not limited to, *P. falciparum, P. vivax, P. ovale*, and *P. malariae*, one or more recombinant *Plasmodium* species or strains, one or more sporozoite strains, or a combination thereof. The priming antigenic component of the priming composition can include one or more sporozoites from one or more additional malaria species and/or sub-species or can include one or more sporozoites from one or more malaria species and/or sub-species instead of *P. falciparum, P. vivax, P. ovale*, and *P. malariae*. In some embodiments, one or more of the sporozoites are attenuated.

In other embodiments, the priming antigenic component is not a wildtype or an attenuated *Plasmodium* parasite, but is an antigen derived from one or more *Plasmodium* species that causes a malaria infection, for example, *P. falciparum, P. vivax, P. ovale*, and *P. malariae*. In such embodiments, the priming antigenic component is one or more *Plasmodium* proteins or portion(s) thereof or a nucleic acid molecule that encodes one or more *Plasmodium* proteins or portion(s) thereof.

In some embodiments, the priming antigenic component is a DNA polynucleotide (e.g., a plasmid) or an RNA polynucleotide that encodes or expresses a *Plasmodium* circumsporozoite protein (CSP) or a peptide or polypeptide comprising an antigenic portion of a *Plasmodium* CSP (e.g., a CSP fragment), with or without another *Plasmodium* protein or antigenic fragment thereof. In other embodiments, the priming antigenic component of the priming composition is (i) a protein, polypeptide, or antigenic fragment thereof and/or (ii) a virus-like particle delivered antigen, which comprises a *Plasmodium* CSP or an antigenic fragment thereof, with or without another *Plasmodium* protein or antigenic fragment thereof.

Other examples of proteins or portion(s) thereof that may be used as a priming antigenic component in accordance with the embodiments described herein include, but are not limited to, one or more non-CSP antigens which may mediate protection without inducing CSP-specific immunity (Gruner et al.; Kumar et al. 2009; Mauduit et al. 2009; Mauduit et al. 2010). In addition to CSP, the non-CSP antigens include more than about 2000 pre-erythrocytic proteins that may or may not be targeted by pre-erythrocytic humoral and CTL responses. For example, of these more than about 2000 additional antigens, specific antigens that the antigenic subunit component of the malaria vaccine compositions can target include, but are not limited to, thrombospondin-related adhesive protein (TRAP/SSP2) (Pearson et al. 2015; Longley et al.), *Plasmodium falciparum* LSA-1 (PfLSA1), *Plasmodium falciparum* AMA1 (PfAMA1), CelTOS (Mishra et al.), PfLSA3 (Sauzet et al.), the ortholog of PBANKA_071450 (Lau et al.), the ortholog of PY03470 (Shuaibu et al. 2010), the ortholog of PY06414/TMP21 (Chen et al.), the ortholog of Py03011 (Limbach et al.), the ortholog of Py03424 (Limbach et al.), the ortholog of Py03661 (Limbach et al.), the ortholog of PY01316 (Haddad et al.), the ortholog of Py01157 (Zhang et al.), and/or a combination thereof. In some embodiments, the priming antigenic component is selected from a) *Plasmodium falciparum* circumsporozoite protein; b) *Plasmodium vivax* circumsporozoite protein; c) *Plasmodium falciparum* TRAP/SSP2 protein; d) *Plasmodium vivax* TRAP; e) *Plasmodium falciparum* AMA1; and f) *Plasmodium falciparum* LSA-1.

In one embodiment, the priming composition includes a priming antigenic component including a plasmid or nanoplasmid constructed to include a DNA molecule (e.g., a gene or minigene) that encodes a *Plasmodium falciparum* circumsporozoite protein (PfCSP) or antigenic fragment thereof. When delivered to the nucleus of a host cell, the plasmid or nanoplasmid expresses the PfCSP or antigenic fragment thereof and is then presented with the cell's MHC to prime the immune response.

In other embodiments, the priming antigenic component of the priming composition is a DNA polynucleotide or an RNA polynucleotide, which encodes a protein or peptide from another liver-tropic pathogen such as hepatitis A virus, hepatitis B virus, hepatitis C virus, hepatitis D virus, hepatitis E virus, Yellow Fever, or Dengue virus types 1, 2, 3, or 4. In still further embodiments, the priming antigenic component of the priming composition is a peptide, protein or polypeptide and/or the virus-like particle delivered antigen and comprises a protein from another liver-tropic pathogen such as hepatitis A virus, hepatitis B virus, hepatitis C virus, hepatitis D virus, hepatitis E virus, Yellow Fever, or Dengue virus types 1, 2, 3, or 4. In certain embodiments, the priming antigenic component of the priming composition is a non-structural protein (e.g., NS3, NS4, NS5A, NS5B) or a p7 protein of hepatitis C virus (or an antigenic portion thereof).

In other embodiments, the priming antigenic component of the priming composition is a DNA polynucleotide or an RNA polynucleotide that encodes a protein or peptide (or antigenic portion thereof) associated with liver cancer (e.g., a neoantigen); or is a peptide, protein or polypeptide and/or a virus-like particle delivered neoantigen. In some embodiments, the priming antigenic component is a neoantigen associated with liver cancer or an antigenic fragment thereof. For example, in certain embodiments, the neoantigen or fragment thereof may include, but is not limited to, SSX-2, MUC-1, MAGE-A3/4, NYESO-1, AFP, MAGE-A10, MAGE-A1, MAGE-C1, MAGE-C2, GPC-3, MDK, Survivin, WT-1, SP17, or Annexin-A2 or an antigenic fragment thereof.

According to some embodiments, the priming composition may include a particle-based carrier such as nanoparticles and liposomes, VLPs or viral capsid proteins. Examples of nanoparticle-based carriers that may be used in accordance with the embodiments described herein may include, but are not limited to, polymeric nanoparticles (e.g., polyacrylamide, polyacrylate, chitosan, cellulose, alginate, xanthan gum), dendrimers, inorganic nanoparticles and nanocrystals (e.g., quantum dots, gold, titanium, iron oxide, and other metallic nanoparticles), organic nanocrystals (e.g., polysaccharides), liposomes, micelles; nanosomes, niosomes, microparticles and other suitable nanoparticles or structures. In some embodiments, the particle-based carrier is selected for facilitating the administration of the priming composition orally, parenterally (e.g., intravenous, intramuscular, subcutaneous administration), transdermally (via a patch or other topical administration; or via other methods such as gene gun administration), transmucosally, or other suitable administration. Additional examples of particle-based carriers are described in detail below. In one embodiment, the priming composition is loaded onto a gold bead or other suitable carrier for use with cartridges of a gene gun.

Trapping Compositions

The technology of the present disclosure uses a "trapping" vaccine composition (or second composition or second dose) such that an antigenic component of the trapping vaccine composition is delivered to the liver and is capable of inducing an immune response in the liver. According to the embodiments described herein, a trapping vaccine composition includes a trapping antigenic component, a protective component (e.g., a carrier), and a liver cell-targeting component, each of which is further described herein.

The technology of the present disclosure is advantageous over previous prime and trap strategies due to the use of vaccine compositions that deliver an antigenic component as part of the "trap" to the liver without also delivering a sporozoite in conjunction with the trap. Thus, the trapping compositions described herein are capable of inducing a protective immune response in the liver without administration of a sporozoite.

In certain embodiments, the trapping antigenic component is able to elicit a tissue-specific immune response when administered to that tissue. In certain embodiments, the trapping vaccine composition is a liver-targeting composition that elicits a liver-specific immune response to the trapping antigenic component.

In certain embodiments, the trapping antigenic component may be a protein, peptide, or antigenic portion thereof expressed by a virus, a virus-like particle (VLP), or a plasmid; a plasmid that encodes a nucleic acid molecule, a deoxynucleic acid (DNA) molecule (or polynucleotide), a ribonucleic acid (RNA) molecule (or polynucleotide); or a protein, a polypeptide, a peptide, or antigenic portions or combinations thereof. In some embodiments where the trapping antigenic component is a virus, a VLP, or plasmid, said virus, VLP, or plasmid comprises or encodes the nucleic acid molecule, DNA molecule or polynucleotide, RNA molecule or polynucleotide, protein, or peptide used as a trapping antigenic component. In certain embodiments, the trapping antigenic component may also need a delivery vehicle or carrier to effect expression of the antigen. For example, a vaccine composition that uses a RNA or DNA molecule (e.g., as part of a plasmid) for the antigenic component needs to be delivered intracellularly to the cytoplasm or nucleus, respectively, of a target cell. Thus, in some embodiments, the RNA or DNA molecule may be delivered by a viral vector, a VLP, a nanoparticle, or any other suitable delivery vehicle or carrier (e.g., particles, liposomes, nanosomes, niosomes, microparticles). Consequently, in certain embodiments, the trapping antigenic component can be a deoxyribonucleic acid (DNA) polynucleotide (e.g., a plasmid), a ribonucleic acid (RNA) polynucleotide, a protein or a polypeptide, a virally-vectored antigen, a virus-like particle delivered antigen, a nanoparticle, a fragment thereof, a subunit thereof, and/or a combination thereof.

In some embodiments, the nucleic acid molecule, DNA molecule, RNA molecule, protein, or peptide used as a trapping antigenic component may be derived from a liver-tropic pathogen that gives rise to a hepatotropic infection or a pathogenic marker expressed on liver cells (e.g., cancer-specific markers), examples of which are discussed below.

In some embodiments, the trapping antigenic component is an antigen derived from one or more *Plasmodium* species that causes a malaria infection, for example, *P. falciparum, P. vivax, P. ovale*, and *P. malariae*. In such embodiments, the trapping antigenic component is one or more *Plasmodium* proteins or portion(s) thereof or a nucleic acid molecule that encodes one or more *Plasmodium* proteins or portion(s) thereof.

In some embodiments, the trapping antigenic component is a DNA polynucleotide (e.g., a plasmid) or an RNA polynucleotide that encodes or expresses a *Plasmodium* circumsporozoite protein (CSP) or a peptide or polypeptide comprising an antigenic portion of a *Plasmodium* CSP (e.g., a CSP fragment), with or without another *Plasmodium* protein or antigenic fragment thereof. In other embodiments, the trapping antigenic component of the trapping composition is (i) a protein, polypeptide, or antigenic fragment thereof and/or (ii) a virus-like particle delivered antigen, which comprises a *Plasmodium* CSP or an antigenic fragment thereof, with or without another *Plasmodium* protein or antigenic fragment thereof.

Other examples of proteins or portion(s) thereof that may be used as a trapping antigenic component in accordance with the embodiments described herein include, but are not limited to one or more non-CSP antigens which may mediate protection without inducing CSP-specific immunity (Gruner et al.; Kumar et al.; Mauduit et al.). In addition to CSP, the non-CSP antigens include more than about 2000 pre-erythrocytic proteins that may or may not be targeted by pre-erythrocytic humoral and CTL responses. For example, of these more than about 2000 additional antigens, specific antigens that the antigenic subunit component of the malaria vaccine compositions can target include, but are not limited to, thrombospondin-related adhesive protein (TRAP/SSP2) (Pearson et al and Longley et al.), *Plasmodium falciparum* LSA-1 (PfLSA1), *Plasmodium falciparum* AMA1 (PfAMA1), CelTOS (Mishra et al.), PfLSA3 (Sauzet et al.), the ortholog of PBANKA_071450 (Lau et al.), the ortholog of PY03470 (Cherif et al.), the ortholog of PY06414/TMP21 (Chen et al.), the ortholog of Py03011 (Limbach et al.), the ortholog of Py03424 (Limbach et al.), the ortholog of Py03661 (Limbach et al.), the ortholog of PY01316 (Haddad et al.), the ortholog of Py01157 (Zhang et al.), and/or a combination thereof. In some embodiments, the trapping antigenic component is selected from a) *Plasmodium falciparum* circumsporozoite protein; b) *Plasmodium vivax* circumsporozoite protein; c) *Plasmodium falciparum* TRAP/SSP2 protein; d) *Plasmodium vivax* TRAP; e) *Plasmodium falciparum* AMA1; and f) *Plasmodium falciparum* LSA-1.

In one embodiment, the trapping composition includes a trapping antigenic component including a plasmid or nanoplasmid constructed to include a DNA molecule (e.g., a gene or minigene) that encodes a *Plasmodium falciparum* circumsporozoite protein (PfCSP) or antigenic fragment thereof. When delivered to the nucleus of a host cell, the plasmid or nanoplasmid expresses the PfCSP or antigenic fragment thereof and is then presented with the cell's MHC to prime the immune response.

In other embodiments, the priming antigenic component of the priming composition is a DNA polynucleotide or an RNA polynucleotide, which encodes a protein or peptide from another liver-tropic pathogen such as hepatitis A virus, hepatitis B virus, hepatitis C virus, hepatitis D virus, hepatitis E virus, Yellow Fever, or Dengue virus types 1, 2, 3, or 4. In still further embodiments, the priming antigenic component of the priming composition is a peptide, protein or polypeptide and/or the virus-like particle delivered antigen and comprises a protein from another liver-tropic pathogen such as hepatitis A virus, hepatitis B virus, hepatitis C virus, hepatitis D virus, hepatitis E virus, Yellow Fever, or Dengue virus types 1, 2, 3, or 4. In certain embodiments, the priming antigenic component of the priming composition is a non-structural protein (e.g., NS3, NS4, NS5A, NS5B) or a p7 protein of hepatitis C virus (or an antigenic portion thereof).

In other embodiments, the priming antigenic component of the priming composition is a DNA polynucleotide or an RNA polynucleotide that encodes a protein or peptide (or antigenic portion thereof) associated with liver cancer (e.g., a neoantigen); or is a peptide, protein or polypeptide and/or a virus-like particle delivered neoantigen. In some embodiments, the priming antigenic component is a neoantigen associated with liver cancer or an antigenic fragment thereof. For example, in certain embodiments, the neoantigen or fragment thereof may include, but is not limited to, SSX-2, MUC-1, MAGE-A3/4, NYESO-1, AFP, MAGE-A10, MAGE-A1, MAGE-C1, MAGE-C2, GPC-3, MDK, Survivin, WT-1, SP17, or Annexin-A2 or an antigenic fragment thereof.

In certain embodiments, the trapping antigenic component of the trapping composition also includes one or more tags that are added to the antigenic component resulting in a tagged-polypeptide or tagged-peptide. In some embodiments, the tag is a ubiquitin tag however, in other embodiments, the antigenic component can include a different tag or additional tags, such as a poly-histidine (e.g., 6x-HIS), chitin binding protein (CBP), maltose binding protein (MBP), streptavidin (SA), glutathione-S-transferase (GST), calmodulin-tag, E-tag, FLAG-tag, hemagglutinin tag (HA), c-myc tag, LC3 tag and any other tag suitable for conjugation to a polypeptide and useful with the present disclosure.

According to the embodiments described herein, the trapping composition also comprises a protective component that acts as a carrier to protects the antigenic component after administration until it reaches the liver, such as in the bloodstream or gastrointestinal system. In some embodiments, the protective component is a non-natural or synthetic material. Non-limiting examples of protective component carriers include, but are not limited to particle-based carriers such as nanoparticles and liposomes, VLPs or viral capsid proteins, and viruses. In certain embodiments, the protective component is a particle-based carrier, examples of which include, but are not limited to, polymeric nanoparticles (e.g., polyacrylamide, polyacrylate, chitosan, cellulose, alginate, xanthan gum), dendrimers, inorganic nanoparticles and nanocrystals (e.g., quantum dots, gold, titanium, iron oxide, and other metallic nanoparticles), organic nanocrystals (e.g., polysaccharides), liposomes, micelles; nanosomes, niosomes, microparticles and other suitable nanoparticles or structures. The protective component can coat, encapsulate, encompass, or envelop the antigenic component. In some cases, the coating, encapsulating, encompassing, or enveloping protective component is permeable. Alternatively, the protective component can be intercalated with the antigenic component or form a polyplex with the antigenic component.

In some embodiments, the protective component includes one or more nanoparticle based carriers. Nanoparticle-based protective methods are described, for example, in Kim et al., Zhang et al., Gorad et al., Nurunnabi et al., Bae et al., and Kren et al., the entireties of which are incorporated herein by reference. In some embodiments, the protective component includes one or more nanoparticles for facilitating the administration of the trapping composition to the liver of a subject in need thereof. In some embodiments, the protective component is selected for facilitating the administration of the trapping composition orally, parenterally (e.g., intravenous, intramuscular, subcutaneous administration), transdermally (via a patch or other topical administration; or via other methods such as gene gun administration), transmucosally, or other suitable administration.

In some embodiments, the protective component is a chitosan-containing particle or nanoparticle. Chitosan is a particularly suitable polymer for oral and transdermal/mucosal drug delivery due to its properties of mucoadhesivity, permeation enhancement, biocompatibility, biodegradability, and efflux pump inhibition. Non-limiting examples of chitosan-containing particles or nanoparticles suitable for use as a protective component in the trapping compositions described herein include, but are not limited to, (i) chitosan, (ii) chitosan derivatives (e.g., mucoadhesive derivatives) such as Trimethyl chitosan, N-(2-hydroxy)-propyl-3-trimethyl chitosan, N-octyl chitosan, Octadecyl quaternization chitosan, N-carboxymethyl chitosan, N-succinyl chitosan, N-acetylcysteine chitosan, O-carboxymethyl chitosan, Glycol chitosan, N-(2-hydroxy)-propyl-3-trimethylammonium chloride modified chitosan, (iii) modified chitosan for improved environmental responsiveness in conditions related to pH, temperature, enzyme and magnetic field (e.g., chitosan embedded or grafted with arginine, lysine, vitamin B12, succinylation, GFLG tetrapeptide, EDTA, DMMA, CA, Poly(2-(diisopropylamino)ethyl methacrylate), Poly(methyl methacrylate), Polyacrylic acid (PAA), pNIPAA, pluronics, iron oxide).

In some embodiments, the protective component is a non-chitosan-containing particle or nanoparticle. Non-limiting examples of nanoparticles that may be included as the protective component include, but are not limited to, hydroxypropyl methylcellulose phthalate, tripolyphosphate, cholic acid, superparamagnetic iron oxide, albumin, branched polyethyleneimine, heparin-taurocholic acid, aptamers, markers, as well as any others known to those of ordinary skill in the art including those discussed above.

According to the embodiments described herein, the trapping composition also comprises a liver cell-targeting component to direct the trapping composition to the liver and thereby causing the trapping antigen component to be delivered and/or expressed in the liver. In certain embodiments, the liver cell-targeting component is a material that can coat or otherwise be conjugated to the protective material (e.g., the nanoparticles discussed above). Non-limiting examples of liver cell-targeting components that may be used in the trapping composition include, but are not limited to, an asialoorasomucoid (ASOR) polypeptide, a N-acetyl-galactosamine (NAG) sugar, an asialotrianntenary (A3) polypeptide or a hyaluronan (HA) polypeptide. Nanocapsules coated with ASOR, NAG, A3, arabinogalactan or another synthetic or naturally occurring galactose-presenting molecule specifically target hepatocytes via asialoglycoprotein receptors (ASGPr), while nanocapsules coated with HA, NAG or mannan specifically target liver sinusoidal endothelial cells (LSECs) via the hyaluronan, NAG or mannose receptors, respectively.

The liver-cell targeting component may or may not have the characteristic of specifically binding cells in the liver. In some embodiments, the liver-cell targeting component facilitates the trapping vaccine composition through the gastrointestinal system to the blood stream. In other embodiments, the liver cell-targeting component specifically targets liver cells. In certain embodiments, the liver-cell targeting components include bile-acid molecules. Non-limiting examples of bile-acid molecules that may be used include, but are not limited to, taurocholic acid, glycocholic acid, derivatives of cholic acid, taurochenodeoxycholic acid, glycochenodeoxycholic acid, derivatives of chenodeoxycholic acid, deoxycholic acid, lithocholic acid, cholic acid, chenodeoxycholic and deoxycholic acids.

According to the embodiments described herein, the liver cell-targeting component is conjugated to the protective component, such as a nanoparticle, to form a liver cell-targeting vehicle that carries the trapping antigen component. Accordingly, in certain embodiments, the trapping composition includes liver cell-targeting vehicles selected from one or more of: a) bile acid-conjugated, chitosan-containing particles or nanoparticles (e.g., plasmid DNA or mRNA as chitosan particles coated with or formulated with bile acids); b) non-bile acid-conjugated, chitosan-containing particles or nanoparticles coated with or formulated with a different liver-targeting formulation; c) bile acid-conjugated, non-chitosan-containing particles or nanoparticles (e.g., plasmid DNA or mRNA with branched polyethyleneimine followed by coating the surface with bile acid conjugates); and d) non-bile acid-conjugated, non-chitosan-containing particles or nanoparticles coated with or formulated with a different liver-targeting formulation.

In the embodiments discussed above, the trapping composition does not include a sporozoite or any other wildtype or attenuated *Plasmodium* parasite, and in certain embodiments, the trapping composition is a nucleic acid vaccine composition (e.g., a DNA vaccine or RNA vaccine) used in a nucleic acid-only-based vaccine regimen. In certain alternative embodiments, the trapping composition may also include a wildtype or an attenuated *Plasmodium* parasite. In some embodiments, the wild-type or attenuated *Plasmodium* parasite is a wild-type or attenuated sporozoite from a species of malaria. For example, the trapping antigenic component of the trapping composition includes one or more wild-type or attenuated sporozoites selected from one or more *Plasmodium* species, such as but not limited to, *P. falciparum, P. vivax, P. ovale*, and *P. malariae*, one or more recombinant *Plasmodium* species or strains, one or more sporozoite strains, or a combination thereof. The trapping antigenic component of the trapping composition can include one or more sporozoites from one or more additional malaria species and/or sub-species or can include one or more sporozoites from one or more malaria species and/or sub-species instead of *P. falciparum, P. vivax, P. ovale*, and *P. malariae*. In some embodiments, one or more of the sporozoites are attenuated.

As discussed above, the trapping composition may include a virus to be used as a vector as part of the trapping antigenic component or as a protective component. Thus, in some embodiments, the trapping composition includes a viral vector encoding an antigenic component. Non-limiting examples of viruses or viral vectors that may be used in accordance with the embodiments described herein include, but are not limited to, an adeno-associated viral vector, a yellow fever viral vector, an adenoviral vector, a modified vaccinia virus ankara, or a combination thereof.

Also as discussed above, the vaccine compositions used in accordance with the embodiments described herein are part of a tissue-specific vaccine regimen. As described herein, a tissue-specific vaccine refers to a vaccine that targets and/or operates in a tissue-specific manner, thereby mounting an immune response by cells residing in a specific tissue. For example, the vaccines described herein can provide pre-erythrocytic protection by targeting Trm cells to reside in the liver. Thus, according to certain embodiments, the tissue-specific vaccines and regimens include vaccine compositions that are specific for the subject's liver tissue.

Vaccine compositions of the present technology are designed to elicit an immune response to one or more antigens such as those described above. For example, the priming antigenic component and/or the liver-specific trapping antigenic component may be designed to present one or more antigens for immune cell targeting. For example, the priming composition and/or trapping composition may include a priming and/or trapping antigenic component that includes one antigen, two antigens, three antigens, four antigens, five antigens, six antigens, eight antigens, nine antigens, ten antigens, more than ten antigens, 15 antigens, more than 15 antigens, 20 antigens, or more than 20 antigens. In some embodiments, the priming and/or trapping antigenic components include a greater number of antigens when intended for use in humans compared to those intended for use in other non-human subjects due to the plurality of human major histocompatibility complex (MHC) genes in humans compared to mice.

In some embodiments, the priming and trapping antigenic components are priming and trapping DNA and/or RNA vaccines, respectively, resulting in a nucleic-acid only vaccine. The DNA and/or RNA vaccines can include one or more DNA and/or RNA sequences, such as antigen-coding sequences as discussed above. In some embodiments, the one or more DNA and/or RNA sequences are the same as one another, and, in other embodiments, the one or more DNA sequences are different from one another. For example, a priming DNA and/or RNA vaccine may include a first group of multiple different priming DNA and/or RNA sequences administered in parallel (e.g., a group comprising two or more different sequences, three or more different sequences, four or more different sequences, four or more different sequences, five or more different sequences, six or more different sequences, seven or more different sequences, eight or more different sequences, nine or more different sequences, ten or more different sequences, twenty or more different sequences, thirty or more different sequences, forty or more different sequences, fifty or more different sequences, sixty or more different sequences, seventy or more different sequences, eighty or more different sequences, ninety or more different sequences, 100 or more different sequences, more than 100 different sequences, more than 1000 different sequences, a plurality of different sequences, and so on). Likewise, the trapping DNA and/or RNA vaccine may include a second group of multiple different boosting DNA and/or RNA sequences administered in parallel. The first group of sequences in the priming DNA and/or RNA vaccine and the second group of sequences in the trapping DNA and/or RNA vaccine may be the same group of sequences, a different group of sequences, or a combination of some of the same sequences and some different sequences. In addition, the one or more antigen-coding sequences can include one or more adjacent DNA sequences that are the same or different from one another. For example, in some embodiments, a DNA and/or RNA sequence in the first DNA and/or RNA vaccine may have the same antigen-coding sequence as a DNA and/or RNA sequence in the second DNA and/or RNA vaccine but may differ with respect to a sequence adjacent to the antigen-coding sequence. For example, the adjacent promoter sequence may differ based on the target delivery method or target tissue (e.g., a DNA priming in the skin may require a CMV promoter, while a liver-specific boosting dose may require a different liver-specific promoter). For example, in certain embodiments, a promotor may be derived from hepatitis B virus or other hepatotropic viruses. In some embodiments, a promotor may be Alpha I antitrypsin. In certain embodiments, a promotor may be a chimeric promoter.

The one or more antigens included as part of the antigenic component of the priming and trapping vaccine compositions of the present technology can activate one or more CD8+ T cells which detect and eliminate one or more liver cells infected with the one or more antigens (Longley et al.).

In some embodiments, vaccine compositions of the present disclosure may optionally include an adjuvant or adjuvant-encoding plasmids. For example, the priming composition and/or trapping composition of the vaccine compositions can be administered to a subject in need thereof (e.g., a mammal) with the adjuvant. In some embodiments, the adjuvant is an *E. coli* heat-labile toxin-encoding plasmid (e.g., heat-labile lymphotoxin).

The administration of the trapping composition induces trafficking of one or more cells (e.g., immune cells such as antigen presenting cells, T cells, or the like) to the subject's liver.

Unlike conventional malaria vaccines, malaria vaccine compositions of the present technology do not necessarily induce an antibody response in the subject against one or more components of the malaria vaccine itself following administration. In this way, the present technology results in malaria vaccine compositions, malaria vaccine regimens, and malaria vaccine methods that are more efficacious when compared to conventional malaria vaccines. In some embodiments, the antibody response to the priming composition and/or the trapping composition in the subject following administration of one or more of the malaria vaccine compositions is not induced in the mammal following administration of the priming composition and/or the trapping composition. However, in other embodiments, the antibody response to the priming composition and/or the trapping composition in the subject following administration of one or more of the malaria vaccine compositions is induced in the mammal following administration of the priming composition and/or the trapping composition. In these embodiments, the subject's antibody response to the priming composition and/or the trapping composition may be reduced compared to a subject who received a conventional malaria vaccine.

Vaccination Regimens and Methods of Vaccination

The prime-and-trap malarial vaccination regimens are taught in in PCT application NO. PCT/US19/13114 filed on Jan. 10, 2019, which claims priority to U.S. Provisional application No. 62/615,755 filed Jan. 10, 2018, all of which are incorporated herein by reference.

In some embodiments, the methods of vaccinating subjects with one or more of the vaccine compositions and/or vaccination regimens of the present technology result in tissue-specific vaccination in a subject. As used herein the term "subject" or "subjects" refers to an animal, a mammal, a non-human primate, and/or a human in both the singular and the plural form (e.g., more than one). In certain embodiments, the tissue is the subject's liver, and/or the vaccination is against malaria, such as the plurality of species and sub-species of malaria described herein. In other embodiments, the vaccination is against another liver-tropic pathogen or a liver cancer marker.

In one embodiment, the methods for tissue-specific vaccination in a subject includes administering a first priming composition comprising an antigenic subunit component to the subject and administering a second trapping composition comprising a tissue-specific component of an infectious organism to the subject.

According to some embodiments, a vaccination regimen may include two doses: a first dose comprising a priming composition (such as those described above) followed by a second dose comprising a trapping composition (such as those described above).

According to some embodiments, a vaccination regimen may include two doses: a first dose comprising a first trapping composition (such as those described above) followed by a second dose comprising a second trapping composition (such as those described above). In such embodiments, the first trapping composition acts as the priming composition, and both doses are administered orally or parenterally. In these embodiments, gene gun administration of a first dose comprising a priming composition is not required. In these embodiments, the first trapping composition and the second trapping composition are the same. In other embodiments, the first trapping composition and the second trapping composition are different. In certain embodiments, the first trapping composition and the second trapping composition are both administered orally. In further embodiments, the first trapping composition and the second trapping composition are administered parenterally. In yet further embodiments, the first trapping composition is administered orally, and the second trapping composition is administered parenterally. In still further embodiments, the first trapping composition is administered parenterally, and the second trapping composition is administered orally.

In another embodiment, the vaccination regimen involves three doses: a first dose comprising a priming composition such as those described above, a second dose comprising a trapping composition such as those described above), and a third dose comprising a boosting composition that includes a priming antigenic component and/or trapping antigenic component (e.g., like those described above). In some embodiments, the boosting composition is the same composition as the priming composition. In other embodiments, the boosting composition is the same composition as the trapping composition. The boosting composition (i.e., the third dose) is administered in between the priming and trapping compositions. Thus, in accordance with the prime and trap strategy, the priming composition is administered to the subject, followed by the boosting composition, which is then followed by the trapping composition.

Methods of vaccinating subjects with one or more of the vaccine compositions and/or vaccination regimens of the present technology also include methods for increasing a number of resident memory T cells (e.g., liver Trms) in a subject. In certain embodiments, such methods include a step of administering a priming composition to the subject as a first dose. Following administration of the priming composition, such methods for vaccinating the subject include a step of administering the trapping composition as a second dose. In other embodiments, methods of vaccinating a subject include a first step of administering a priming composition to the subject as a first dose, followed by a second step of administering a boosting composition as a second dose, followed by a third step of administering a trapping composition as a third dose.

Following administration of the two or more vaccine compositions to the subject, a number of resident memory T cells in the subject's liver are increased. For example, the number of resident memory T cells in the subject's liver are increased following administration of the priming and trapping (and optionally, the boosting) compositions of the vaccine compositions.

According to the embodiments described herein, administration of the priming composition (and optionally, the boosting composition) may be provided by any suitable administration method known in the art. In some embodiments, the priming composition may be administered to a subject via administration to the skin. In some embodiments, such administration is intradermal administration, transdermal administration, or epidermal administration. In some embodiments, the administration is intranasal or mucosal administration. In certain embodiments, the administration is by particle-mediated epidermal delivery (PMED) or gene gun administration. In certain embodiments, administration is via in vivo electroporation, parenteral administration (e.g., intramuscular injection, subcutaneous injection, intravenous injection, micro-needle injection), micro-array delivery, or via a transdermal method (e.g., a transdermal patch). The gene gun method, and other methods described herein, can be combined with Highly Parallel Immunization (HPI) technology described in WIPO Patent Publication No 2017/024084 (PCTUS2016/045439) which is incorporated herein by reference in its entirety) which could result in the vaccine compositions achieving a greater T cell repertoire without immune "skewing" compared to methods in the absence of HPI technology.

In one embodiment, the priming composition is administered by a gene gun. The gene gun method is well-known in the art and are described in Fuller et al. 2006, the entireties of which are incorporated herein by reference. In some embodiments, the gene gun method includes combining the priming composition (or boosting composition) with a plurality of gold beads having a diameter of about 1 µm. The gold beads serve as a scaffold for the DNA and/or RNA polynucleotide component(s) of the vaccine compositions that can be present in the priming composition (or boosting composition). Once combined with the plurality of gold beads, the scaffold (e.g., gold beads and polynucleotides) are delivered sub-dermally to the subject in need thereof using a pulse of helium gas. Amounts of gold beads, DNA and/or RNA polynucleotides, helium gas, delivery parameters such as pressure, and additional techniques associated with the gene gun technology are readily be determined. Unlike other methods of delivering polynucleotides to a subject (e.g., delivery of naked DNA), the gene gun method includes delivery of at least about 10-fold, about 100-fold, about 1000-fold, or about 10,000-fold less DNA to the subject in need thereof. Without intending to be bound by any particular theory, delivering the priming composition (or boosting composition) using the gene gun method is thought to activate one or more dendritic cells to induce an antigen-specific response in the subject to the plurality of expression signals encoded in the DNA and/or RNA polynucleotide.

According to the embodiments described herein, administration of the trapping vaccine composition (and optionally, the boosting composition) include oral administration, skin administration, intravenous administration, intraperitoneal administration, and intramuscular administration. The trapping vaccine compositions (or the boosting composition) may have the advantage of being orally deliverable, e.g., oral delivery of malarial vaccine-containing particles conjugated to bile acids which enter the enterohepatic circulation and thereby traffic to the liver. The particles may be in the form of nanoparticles such as those described above. In this regard, liver-specific promoters on plasmids carried by bile acid-conjugated nanoparticles to drive liver-specific expression and by inclusion of miRNA or other inhibitor components to decrease off-target expression in the GI tract of elsewhere may be employed.

By virtue of delivering the liver-targeting trapping vaccine composition orally or parenterally as described in detail above, the vaccine regimens and methods of vaccination described herein include solely nucleic acid molecule vaccine compositions (i.e., DNA-only or RNA-only vaccine compositions) without the need for administering a sporozoite to the subject. This reduces the immunogenic burden on the subject and increases the efficacy and safety of the vaccination.

Regardless of the vaccine regimen or methods of vaccination described herein, the priming composition is administered to the subject before the trapping composition. In some embodiments, in any of these malaria vaccine regimens, the priming composition can be administered to the subject at least one day, at least two days; at least three days, at least four days, at least five days, at least six days, at least seven days, at least ten days, at least two weeks, at least three weeks, at least four weeks, at least six weeks, or at least eight weeks before the trapping composition is administered to the subject. For example, the priming composition is administered to the subject on day 0 and the trapping composition is administered to the subject on day 28 (e.g., 28 days after administration of the priming composition). As discussed above, a third composition is optionally administered to the subject on day 2 (e.g., 2 days after administration of the priming composition) and, includes but is not limited to, a DNA polynucleotide and/or one or proteins, such as those described herein.

The vaccine compositions described herein (e.g., priming composition, trapping composition, and optionally, boosting composition) may be pharmaceutical compositions that include one or more pharmaceutically acceptable carriers. Examples of acceptable carriers include physiologically acceptable solutions, such as sterile saline and sterile buffered saline.

In further embodiments, use of various other adjuvants, drugs or additives with the vaccine compositions, as discussed above, may enhance the therapeutic effect achieved by the administration of the vaccine or pharmaceutical composition. The pharmaceutically acceptable carrier may contain a trace amounts of additives, such as substances that enhance the isotonicity and chemical stability. Such additives should be non-toxic to a human or other mammalian subject in the dosage and concentration used, and examples thereof include buffers such as phosphoric acid, citric acid, succinic acid, acetic acid, and other organic acids, and salts thereof; antioxidants such as ascorbic acid; low molecular weight (e.g., less than about 10 residues) polypeptides (e.g., polyarginine and tripeptide) proteins (e.g., serum albumin, gelatin, and immunoglobulin); amino acids (e.g., glycine, glutamic acid, aspartic acid, and arginine); monosaccharides, disaccharides, and other carbohydrates (e.g., cellulose and derivatives thereof, glucose, mannose, and dextrin), chelating agents (e.g., EDTA); sugar alcohols (e.g., mannitol and sorbitol); counterions (e.g., sodium); nonionic surfactants (e.g., polysorbate and poloxamer); antibiotics; and PEG.

Any immunologic adjuvant that may stimulate the immune system and increase the response to a vaccine, without having any specific antigenic effect itself may be used as the adjuvant. Many immunologic adjuvants mimic evolutionarily conserved molecules known as pathogen-associated molecular patterns (PAMPs) and are recognized by a set of immune receptors known as Toll-like Receptors (TLRs). Examples of adjuvants that may be used in accordance with the embodiments described herein include Freund's complete adjuvant, Freund's incomplete adjuvant, double stranded RNA (a TLR3 ligand), LPS, LPS analogs such as monophosphoryl lipid A (MPL) (a TLR4 ligand), flagellin (a TLR5 ligand), lipoproteins, lipopeptides, single stranded RNA, single stranded DNA, imidazoquinolin analogs (TLR7 and TLR8 ligands), CpG DNA (a TLR9 ligand), Ribi's adjuvant (monophosphoryl-lipid A/trehalose dicorynoycolate), glycolipids (α-GalCer analogs), unmethylated CpG islands, oil emulsion, liposomes, virosomes, saponins (active fractions of saponin such as QS21), muramyl dipeptide, alum, aluminum hydroxide, squalene, BCG, cytokines such as GMCSF and IL-12, chemokines such as MIP 1-α and RANTES, activating cell surface ligands such as CD40L, N-acetylmuramine-L-alanyl-D-isoglutamine (MDP), and thymosin α1. The amount of adjuvant used can be suitably selected according to the degree of symptoms, such as softening of the skin, pain, erythema, fever, headache, and muscular pain, which might be expressed as part of the immune response in humans or animals after the administration of this type of vaccine.

The vaccine compositions containing the antigenic components described herein may be stored as an aqueous solution or a lyophilized product in a unit or multiple dose container such as a sealed ampoule or a vial. In the case of oral administration, the vaccine compositions may be formulated in a capsule that is capable of maintaining particle integrity to allow particle-based carriers to reach the stomach and small intestine. In other embodiments, an orally administered vaccine composition may be a suspension or nanosuspension formulation.

In certain embodiments, the methods of vaccination and/or regimens described herein involve administration of an effective amount (or dosage) or a therapeutically effective amount (or dosage) of a priming composition, a trapping composition, and optionally, a boosting composition. The term "effective amount" as used herein refers to an amount of a compound that produces a desired effect. For example, a population of cells may be contacted with an effective amount of a composition to study its effect in vitro (e.g., cell culture) or to produce a desired therapeutic effect ex vivo or in vitro. An effective amount of a compound may be used to produce a therapeutic effect in a subject, such as preventing or treating a target condition, alleviating symptoms associated with the condition, or producing a desired physiological effect. In such a case, the effective amount of a compound is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the compound (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the compound is administered alone or in combination with another compound, drug, therapy or other therapeutic method or modality. One skilled in the clinical and pharmacological arts will be able to determine an effective amount or therapeutically effective amount through routine experimentation, namely by monitoring a cell's or subject's response to administration of a compound and adjusting the dosage accordingly. For additional guidance, see Remington: The Science and Practice of Pharmacy, 21st Edition, Univ. of Sciences in Philadelphia (USIP), Lippincott Williams & Wilkins, Philadelphia, P A, 2005, which is hereby incorporated by reference as if fully set forth herein.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition. In certain aspects, treatment of malaria means prevention of malaria infection as tested by a sporozoite challenge.

The present technology additionally includes methods associated with the methods of vaccinating subjects with one or more of the vaccine compositions and/or vaccination regimens described above. These additional associated methods include, but are not limited to, methods of evaluating a subject's sera prior to administration of the one or more of the malaria vaccine compositions for reactivity against one or more sporozoites (e.g., pre-immunization sera). By evaluating pre-immunization sera, it is thought that a baseline titer below which the malaria vaccine compositions, regimens, and/or methods may be effective in populations of subjects, such as endemic populations. By identifying one or more baseline titers, a plurality of time periods can be identified by which to begin administering one or more of the malarial vaccine regimens and/or methods of the present technology to the subject. In some embodiments, if the baseline titer is achieved in childhood or at the end of a non-transmission season for malaria, then one or more time periods for vaccination can be identified. Baseline titers can also be combined with a seasonality of malaria to identify one or more time periods for vaccination at or near the relative nadir of sporozoite-specific antibody immunity. In some embodiments, the subject's humoral response can be induced following administration of one or more doses of the malaria vaccine compositions. Without intending to be bound by any particular theory, it is thought that determining one or more baseline titers and/or one or more time periods for vaccination that are optionally at or near the relative nadir maximizes formation of Trm cells in the subject's liver. It is further thought that subsequent vaccinations could be advantageous to the subject's immunity against malaria as formation of liver Trm would not be adversely affected by an antibody response.

Methods associated with the present technology also include one or more systems for testing whether a subject is protected against a potential malaria infection using one or more T cell antigens. These methods include challenging the subject with one or more sporozoites during an effector cytotoxic T-cell response (e.g., the peak of the response).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, PlasmoDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

From the foregoing, it will be appreciated that specific embodiments of the invention have been described herein for purposes of illustration, but that various modifications may be made without deviating from the scope of the invention. Accordingly, the invention is not limited except as by the appended claims.

EXAMPLES

Example 1: PyCSP Gene Gun and HDT Boosting Provided Complete Protection Against IV Challenge of 100 Wild-Type *P. yoelii* Sporozoites A dose de-escalation study was conducted to determine whether lower doses of PyCSP DNA administered by hydrodynamic transfection (HDT) protects against a challenge with a physiologically-relevant IV dose of *P. yoelii* sporozoites. A schematic depicting experimental overview including timeline is provided in FIG. 1.

Experimental groups were as follows (n=5 per group):
Group 1: Gene gun PyCSP DNA→Day 33 hydrodynamic transfection (3 μg Luc DNA+1×(12 μg) PyCSP DNA)
Group 2: Gene gun PyCSP DNA→Day 33 hydrodynamic transfection (3 μg Luc DNA+0.1×(1.2 μg) PyCSP DNA)
Group 3: Gene gun PyCSP DNA→Day 33 hydrodynamic transfection (3 μg Luc DNA+0.01×(0.12 μg) PyCSP DNA)
Group 4: Hydrodynamic transfection only (3 μg Luc DNA)

Figure 2:
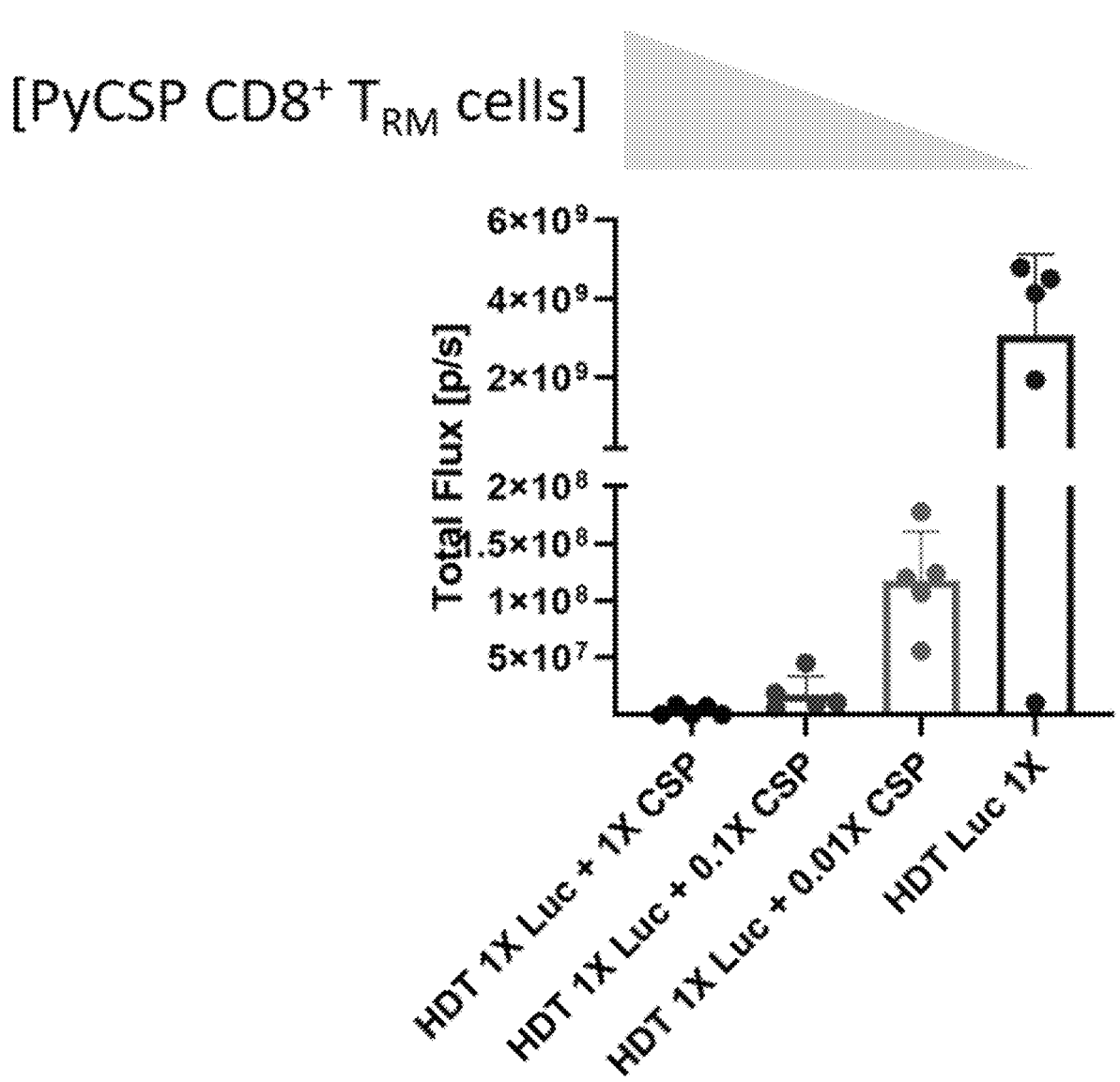
FIG. 2 is a chart quantifying the total flux [p/s] from IVIS imaging following PyCSP HDT.

Inventors performed IVIS imaging following HDT administration. These results demonstrate that the PyCSP HDT dosage was inversely proportional to Luc expression. See FIG. 2. These results suggest that anti-PyCSP CD8+ T cells curtail Luc expression.

Figure 3:
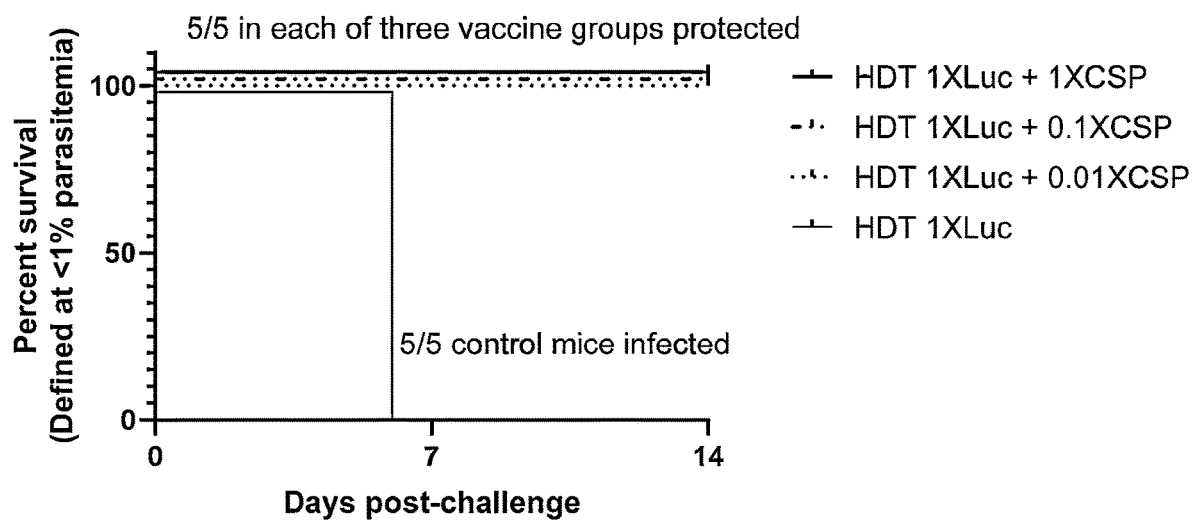
FIG. 3 is a chart quantifying percent survival in groups receiving PyCSP DNA via gene gun followed by HDT versus control.

To determine whether PyCSP DNA gene gun administration followed by HDT resulted in protection, mice were vaccinated using PyCSP DNA by gene gun followed by HDT boosting at the indicated concentrations in FIG. 3.

Experimental groups were as follows (n=5 per group):
Group 1: HDT 1× Luc+1×
Group 2: HDT 1× Luc+0.1×
Group 3: HDT 1× Luc+0.01×
Group 4: HDT 1× Luc 1×

Mice from groups 1-4 were observed for survival rates following an IV challenge with 100 wild-type *P. yoelii* sporozoites. Mice that received PyCSP DNA by gene gun and HDT boosting exhibited 100% protection (15/15 mice) against the IV challenge with 100 wild-type *P. yoelii* sporozoites. No protection was observed in control mice (Luc HDT-only). These data suggest that DNA-only vaccines are possible if DNA is delivered to the liver. Protection was observed at low doses of PyCSP liver expression, indicating it may be possible to achieve protective levels of liver DNA expression using oral DNA nanoparticles.

Example 2: Oral Nanoparticle Delivery of Malaria Vaccine Components

This example describes a study where a nanoparticle delivery method discussed herein is used on murine subjects infected with one or more malaria parasites.

The following experiments represent a set of studies to be performed on mice using nanoparticles. The experiments are designed to be applicable to each formulation of envisioned nanoparticles and may be repeated for different types of nanoparticles.

Experiment 1: In vitro uptake of bile acid-conjugated nanoparticles. This experiment tests whether green fluorescent protein (gfp) and/or luciferase (luc) plasmids driven by a liver-specific promoter are preferentially expressed in hepatocyte-derived cell lines as compared to non-hepatocyte cell lines. CMV promoter-driven plasmids serve as a positive control and empty vector serve as a negative control. HepG2 hepatocyte-derived cells, HepG2-CD81 hepatocyte-derived cells, P815 mastocytoma cells or other cells will be transfected with the corresponding plasmids (alternative positive control) or will be treated with plasmid containing nanoparticles in tissue culture overnight. On the following day(s), GFP and/or luciferase expression will be measured using standard methods. We expect that liver-specific plasmids delivered by bile-conjugated nanoparticles will preferentially express their encoded proteins in hepatocyte derived cells.

Experiment 2: Delivery and Luciferase Expression. This experiment tests the in vivo expression of orally delivered nanoparticles. The nanoparticles (also called gene complex) consists of plasmid DNA condensed with a carrier molecule conjugated to bile acids. This experiment includes IV delivery of test substance to compare with oral delivery. The complex may circulate from the gastrointestinal tract to liver. For this experiment, we will use luciferase (luc) as the test gene. This complex will subsequently carry malaria antigens in future experiments.

Experimental groups are as follows (n=3 mice per group, BALB/cJ):
Group 1: Control (naked) DNA (luc plasmid DNA only)—Oral gavage
Group 2: Control (naked) DNA (luc plasmid DNA only)—IV
Group 3: Gene complex (luc-complex)—Oral gavage
Group 4: Gene complex (luc-complex)—IV
Group 5: Naïve
Experimental schedule is as follows:
Day 0—Bile acid-DNA complex/Nanoplasmid administration: Fast mice, inject 100 ul (100 μg of DNA) via oral gavage or IV as per groups above, continue fast.

Day 1, 3, 4, 8, 14—IVIS Bioimaging*: Inject mice (IP) with 100 ul D-luciferin solution (5 mg per mouse). Immediately anesthetize mice using isoflurane and perform IVIS. If, on day 14 mice are still showing significant expression levels, mice will be imaged on day 20 and day 27 as well to determine when total decay of expression occurs. By day 27, inventors do not expect to see any signal, presuming the mice will have made Luc specific CD8 T cells.

Day 27—*Plasmodium yoelii* (strain 17NL luciferase-expressing-non-lethal) Administration: Challenge mice by injecting IV (retro-orbital or tail vein) with *Plasmodium yoelii* Luciferase expressing sporozoites.

Day 30—IVIS Bioimaging: Following IVIS, humanely euthanize mice ($CO_2$ followed by secondary methods) and isolate spleen and blood post euthanasia.

The oral bile-conjugated nanoparticles may induce luciferase expression in the liver, which will be measurable by IVIS.

Experiment 3: Oral Delivery and Protection. This experiment tests if the orally delivered antigen bearing gene complex confers protection in BALB/cJ mice. Inventors will immunize the animals by priming first with CSP DNA (nanoplasmid administration-previously tested malaria antigen) and then boosting with bile acid-CSP DNA complex via oral gavage. CMV and liver-specific promoters will be use in our antigen expression plasmids. Inventors would like to test and see if the liver-specific promoter Ell-pa1AT (Kramer et al. 2003) localizes and enhances antigen expression in the liver only and not in the gut. Inventors aim to trap antigen specific T cells in the liver to promote pre-erythrocytic or liver stage immunity against malaria parasites. Following challenge, inventors will test for protection. The oral bile-conjugated nanoparticles may recruit *Plasmodium*-specific T cells to the liver to remain there as liver Trm cells, which will protect against a subsequent challenge.

Experiment 3a: High-Dose Challenge with IVIS End-Point.
Experimental groups are as follows (n=5 per group):
Group 1: CSP DNA→Gene complex (Luc with CMV promoter)
Group 2: CSP DNA→Gene complex (CSP+Luc with CMV promoter)
Group 3: CSP DNA→Gene complex (Luc with liver-specific promoter)
Group 4: CSP DNA→Gene complex (CSP+Luc with liver-specific promoter)
Experimental schedule is as follows:
Day 0—Nanoplasmid administration: Prime all groups of mice with CSP DNA using gene gun (GG)—intradermal delivery
Day 28—Bile acid-DNA complex administration: Boost with gene-complex via oral gavage as per the above groups
Day 29, 30—IVIS Bioimaging: Ensure expression of luc
Day 56—*Plasmodium yoelii* (strain 17NL luciferace-expressing—non-lethal) Administration: Challenge mice by injecting IV (retro-orbital or tail vein) with 40,000 *Plasmodium yoelii* Luciferase expressing sporozoites.
Day 58—IVIS Bioimaging to test for protection Experiment 3b: Low-Dose Challenge with Blood Smear End-Point. Experiment 3a is repeated with the same groups, except that mice are challenged with 1000 *Plasmodium yoelii* wild-type sporozoites (*Plasmodium yoelii* (strain 17NL—non-lethal; 17XL—lethal) (or PyRAS) Administration) on day 56 and blood smears (by tail prick) will be used to test for protection between days 60-72. Mice are humanely euthanized at the end point of experiment ($CO_2$ followed by secondary methods).

Experiment 3c: Dose De-Escalation Study. This experiment is to test for the best protective oral dose of the antigen bearing complex for use in future experiments. Based on protective outcomes from the above experiments, different doses of the antigen bearing complex are tested in 6 groups of mice: 100 µg, 25 µg, 10 µg, 5 µg, 2 µg, and 1 µg per mouse (n=5 per group). A naive group is also included. Following immunization on day 0 (nanoplasmid administration) and day 28 (bile acid-DNA complex administration), mice are challenged on day 56 by administering 1000 *Plasmodium yoelii* wild-type sporozoites and tested for protection using blood smears between days 60-72. Mice are humanely euthanized at the end point of experiment ($CO_2$ followed by secondary methods).

If the highest does not result in complete protection, this experiment is repeated with higher dosages (2-4 fold increases).

Experiment 3d: Priming Efficiency of Bile Acid-DNA Complex. This experiment compares protective outcomes from priming intradermally with nanoplasmid gene gun (GG) versus oral delivery of bile acid-DNA complex.
Experimental groups are as follows (n=5 per group, will be repeated in males):
Group 1: CSP DNA GG→CSP complex Oral
Group 2: CSP complex Oral→CSP complex Oral
Group 3: CSP complex Oral→No Boost
Group 4: Näive
Experimental schedule is as follows:
Day 0—Bile acid-DNA complex/Nanoplasmid administration: Prime animals as per the groups above by either gene gun or oral gavage.
Day 28—Bile acid-DNA complex administration: Boost with gene-complex via oral gavage as per the above groups.
Day 56—*Plasmodium yoelii* (strain 17NL luciferase-expressing-non-lethal) Administration: Challenge mice by injecting IV (retro-orbital or tail vein) with 1,000 *Plasmodium yoelii* wild-type sporozoites.
Day 60-72—Blood Smears by tail prick: Humanely euthanize mice at the end point of experiment ($CO_2$ followed by secondary methods).

The nanoparticles may or may not be able to prime a durable T cell response. If they do prime such responses, then nanoparticle-only vaccines may be feasible. If they do not prime such responses, then nanoparticle vaccines may be useful as the trapping formulation when preceded by a potent T cell prime such as DNA vaccination by gene gun or viral vector.

Experiment 4: Immunogenicity of bile acid-DNA complex. This experiment tests if the orally delivered malaria antigen bearing complex induces liver resident memory cells (Trm cells). Animals are immunized as per the following groups and Trms are isolated at the end-point for flow cytometry analysis.
Experimental groups are as follows (n=6 per group):
Group 1: CSP DNA GG→CSP complex Oral
Group 2: CSP complex Oral→CSP complex Oral
Group 3: CSP complex Oral→No Boost
Group 4: Näive
Experimental schedule is as follows:
Day 0—Bile acid-DNA complex/Nanoplasmid administration: Prime animals as per the groups above by either gene gun or oral gavage.

Day 28—Bile acid-DNA complex administration: Boost with gene-complex via oral gavage as per the above groups Day 56—FACS: Humanely euthanize mice ($CO_2$ followed by secondary methods). Perfuse and isolate liver and spleen post euthanasia for flow analysis.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A trapping composition comprising:
a trapping antigenic component comprising a nucleic acid molecule encoding a *Plasmodium* protein or an antigenic fragment thereof;

a protective component comprising a nanoparticle; and a liver cell-targeting component conjugated to the protective component to form a liver cell-targeting vehicle capable of delivering the trapping composition to a liver cell or liver tissue, wherein the liver cell-targeting vehicle comprises one or more bile acids conjugated to the nanoparticle to form a bile-acid conjugated nanoparticle.

2. The trapping composition of claim 1, wherein the trapping antigenic component is encompassed by, enveloped by, encapsulated by, coated by, or intercalated with, or forms a polyplex with the protective component.

3. The trapping composition of claim 1, wherein the trapping antigenic component comprises the nucleic acid molecule under the control of a liver-specific promoter.

4. The trapping composition of claim 1, wherein the trapping antigenic component is a virus, a plasmid, a deoxynucleic acid (DNA) molecule, a ribonucleic acid (RNA) molecule, or a plurality thereof.

5. The trapping composition of claim 4, wherein the virus, the plasmid, the deoxynucleic acid (DNA) molecule, the ribonucleic acid (RNA) molecule, or the plurality thereof encodes a protein or a peptide of *Plasmodium falciparum* circumsporozoite protein.

6. The trapping composition of claim 1, wherein the trapping composition is formulated for oral administration.

7. The trapping composition of claim 1, wherein the trapping antigenic component comprises a tag.

8. The trapping composition of claim 1, further comprising:

a priming composition, wherein the priming composition comprises a priming antigenic component, the priming antigenic component comprising a nucleic acid molecule encoding a protein or a peptide of a *Plasmodium* parasite.

9. The trapping composition of claim 8, wherein the priming antigenic component and the trapping antigenic component are the same or different molecules.

10. The trapping composition of claim 8, wherein the priming composition is formulated to be administered to the skin of a mammal.

11. The trapping composition of claim 8, wherein the trapping composition is formulated for oral administration.

* * * * *